US00PP09980P

United States Patent [19]

Meilland

[11] Patent Number: Plant 9,980

[45] Date of Patent: Jul. 29, 1997

[54] FLORIBUNDA ROSE PLANT NAMED 'MEIDEAURI'

[75] Inventor: Alain A. Meilland, Antibes, France

[73] Assignee: The Conard-Pyle Company, West Grove, Pa.

[21] Appl. No.: 663,737

[22] Filed: Jun. 14, 1996

[51] Int. Cl.[6] ..... A01H 5/00

[52] U.S. Cl. ..... Plt./27

[58] Field of Search ..... Plt./1, 22, 27, Plt./26

*Primary Examiner*—Howard J. Locker

*Attorney, Agent, or Firm*—Burns, Doane, Swecker & Mathis, L.L.P.

[57] ABSTRACT

A new and distinct variety of Floribunda rose plant is provided which abundantly forms attractive Rose Bengal blossoms that exhibit a light fragrance. Such blossoms possess a very romantic shape that is similar to that of old roses. The plant exhibits a bushy growth habit. Attractive dense medium green and glossy vegetation is formed. The new variety is particularly well suited for growing as ornamentation in the landscape. The blossoms well resist rain and commonly open completely even under very humid conditionsl Good Resistance to Marssonina and black spot diseases also is provided.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) was the 'Sommerwind' variety (non-patented in the United States). The male parent (i.e., the pollen parent) of the new variety was the product of the cross of the 'Delbir' variety (non-patented in the United States) and the 'Rosamunde' variety (non-patented in the United States). The 'Delbir' variety is marketed under the MILROSE tradmark. The parentage of the new variety can be summarized as follows:

'Sommerwind'×('Delbir'×'Rosamunde').

The seeds resulting from the above pollination were sown and 73 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive Rose Bengal blossoms,
(b) exhibits a bushy growth habit,
(c) exhibits blossoms having a light fragrance,
(d) forms attractive dense medium green and glossy vegetation,
(e) exhibits good resistance to Marssonina and black spot; and
(f) is particularly well suited for growing as ornamentation in the landscape.

The blossoms possess a very romantic shape that is similar to that of old roses.

The new variety has undergone asexual propagation by a number of routes in France, including budding, grafting, and cuttage. The characteristics of the new variety have been found to be strictly transmissible by such asexual propagation from one generation to another in France.

The new variety has been named the 'Meideauri' variety, and is being marketed under the LEONARDO DA VINCI trademark.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during September while growing outdoors on *Rosa froebelii* understock at Le Cannet des Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistals;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — upper surface;

FIG. 15 — illustrates specimens of two leaves with five leaflets — upper surface (left) and under surface (right); and FIG. 16 — illustrates a specimen of a leaf with seven leaflets — under surface.

DETAILED DESCRIPTION

Figures 1, 2, 3, 4, 5, 6, 7, 8, 9, 10, 11, 12, 13, 14, 15, 16:
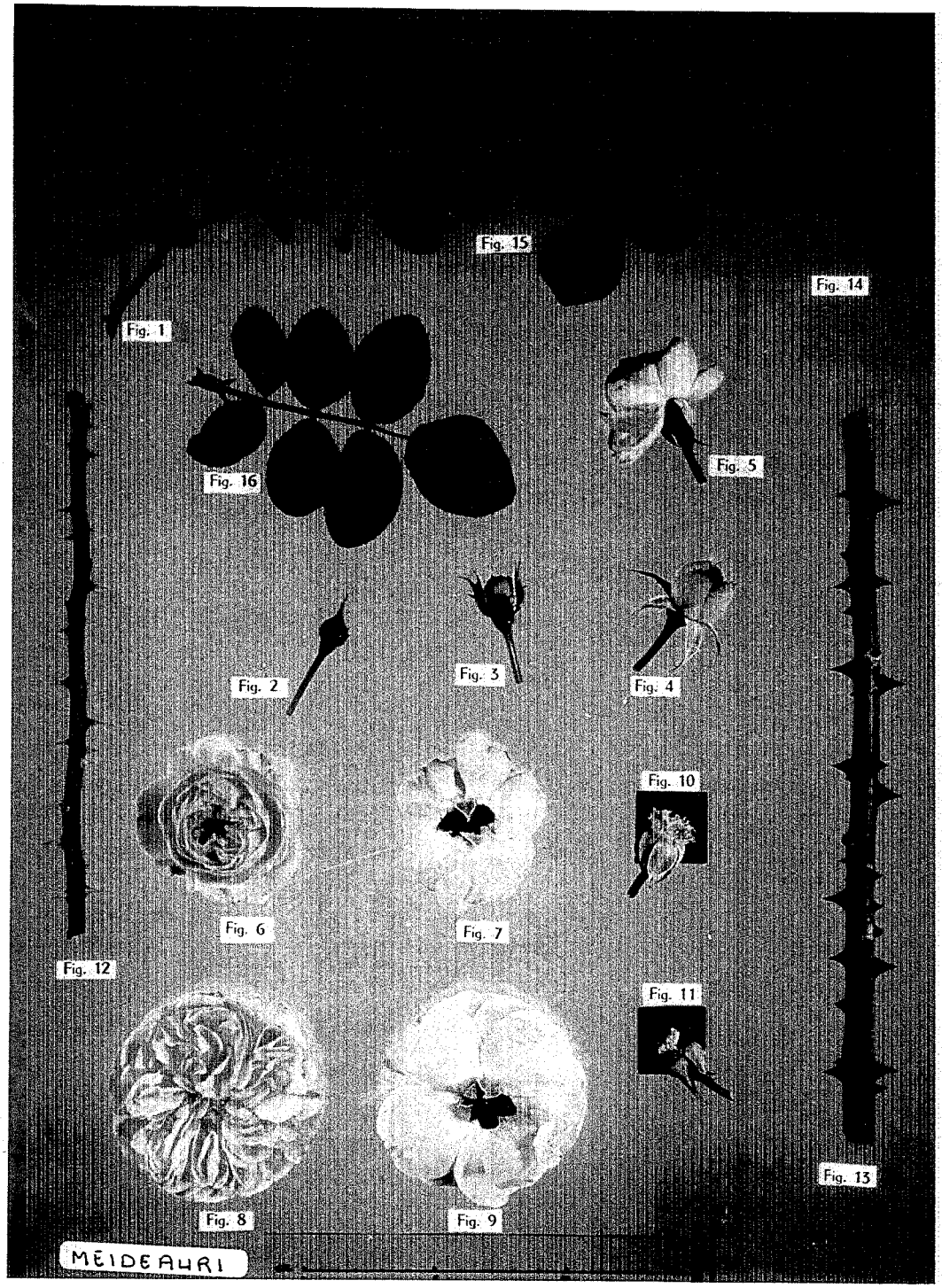

The chart used in the identification of the colors is that of The Royal Horticultural Society (R.H.S. Colour Chart). The terminology which precedes reference to the chart has been added to indicate the corresponding color in more common terms. The description is based on two-year-old specimens of the new variety during September while growing outdoors on *Rosa froebelii understock at Le Cannet des Maures, Var, France.*

Class: Floribunda.

Plant:

*Height.*—Plants commonly achieve a height of approximately 70 to 110 cm. At the end of the growing season.

*Habit.*—Bushy.

Branches:

*Color.*—Young stems: light green, Yellow-Green Group 146D. Adult wood: light green. Yellow-Green Group 144C.

*Thorns.*—Size: medium. Quantity: numerous (as illustrated). Color: somewhat reddish on young stems and greenish-tan on mature wood (as illustrated).

Leaves:

*Stipules.*—Adnate, pectinate, and rather wide and linear.

*Petioles*—Upper surface: striped reddish on young foliage and medium green on adult foliage with more than or less glandular edges. Under suface: light green and bear some small thorns.

*Leaflets.*—Number: 3, 5 and 7 (most often). Shape: oval. Serration: single and regular (as illustrated). texture: leathery. General appearance; dense and glossy foliage. Color (Young foliage): Upper surface: medium green, Green Group 138A, and more or less maculated with reddish coloration. Under surface: light green, Green Group 138B. Color (adult foliage): Upper surface: medium green, Yellow-Green Group 146B. Under surface: light green. Yellow-Green Group 146 C, and widely tinted with reddish coloration.

Inflorescence:

*Number of flowers.*—Commonly approximately 1 to 6 flowers per stem.

*Peduncle.*—Medium green with more or less glandular edges and commonly tinted with reddish coloration, and approximately 3 cm. in length on average.

*Sepals.*—Upper surface: tomentose, and greenish and sometimes tinted with reddish coloration. Under surface: light green and sometimes with appendiculated edges.

*Buds.*—Shape: globular. Length: approximately 2 to 2.5 cm on average. Size: large. Color upon opening: Upper surface: Neyron Rose, Red-Purple Group 58C. Under surface: China Rose, Red-Purple Group 58D.

*Flower.*—Shape: similar to old roses (as illustrated), and opens well even uner very humid conditions. Diameter: approximately 9 to 10 cm. on average. Color (when opening begins): Upper surface: Neyron Rose, Red-Purple Group 58C. Under surface: China Rose, Red-Purple Group 58D. Color (when blooming): Upper surface: light Rose Bengal, Red-Purple Group 57D. Under surface: pearly Rose Bengal, Red-Purple Group 57D. Color (at end of opening): Upper surface: light Rose Bengal, Red-Purple Group 57D. Under surface: pearly Rose Bengal, Red-Purple Group 57D. Fragrance: light. Lasting quality: good. The blossoms commonly last approximately 7 to 10 days on the plant. The blossom life is influenced by the environmental conditions that are encountered. Petal drop: good. Petal form: outer petals are rounded with a cordiform base, and the inner petals are oval with a cuneate base. Petal number: approximately 75 to 80 on average. Stamen number: approximately 91 on average. Anthers: pinkish-ochre in coloration. Filaments: typical and greenish in coloration. Pistils: approximately 115 on average. Stigmas: typical, and greenish in coloration. Styles: greenish in coloration. Receptacle: smooth, medium green in coloration, and in longitudinal section in the shape of a large pitcher.

Development:

*Vegetation.*—Very strong.

*Blooming.*—Continuous and very abundant.

*Aptitude to bear fruit.*—Good.

*Resistance to diseases.*—Very good especially with respect to Marssonina and block spot diseases.

*Blossom resistance to rain.*—Very good.

I claim:

1. A new and distinct variety of Floribunda rose plant characterized by the following combination of characteristics:

(a) forms in abundance attractive Rose Bengal blossoms,
(b) exhibits a bushy growth habit,
(c) exhibits blossoms having a light fragrance,
(d) forms attractive dense medium green and glossy vegetation,
(e) exhibits good resistance to Marssonina and black spot, and
(f) is particularly well suited for growing as ornamentation in the landscape;

substantially as herein shown and described.

* * * * *

MEIDEAURI